United States Patent
Kato et al.

(10) Patent No.: US 6,781,021 B2
(45) Date of Patent: Aug. 24, 2004

(54) METHOD FOR ISOMERIZING HALOGENATED AROMATICS

(75) Inventors: Hajime Kato, Aichi (JP); Kazuyoshi Iwayama, Aichi (JP); Masashi Kato, Aichi (JP); Shinobu Yamakawa, Aichi (JP); Hirohito Okino, Aichi (JP)

(73) Assignee: Toray Industries, Inc. (JP)

( * ) Notice: Subject to any disclaimer, the term of this patent is extended or adjusted under 35 U.S.C. 154(b) by 241 days.

(21) Appl. No.: 10/010,561

(22) Filed: Nov. 8, 2001

(65) Prior Publication Data

US 2002/0132723 A1 Sep. 19, 2002

Related U.S. Application Data

(62) Division of application No. 09/113,587, filed on Jul. 10, 1998, now abandoned.

(30) Foreign Application Priority Data

Jul. 10, 1997 (JP) .............................................. 9-185165
Dec. 5, 1997 (JP) .............................................. 9-335229

(51) Int. Cl.$^7$ .......................... C07C 17/00; C07C 19/08; C07C 21/18; C07C 23/00; C07C 25/00; C07C 22/00; C07C 19/00; C07C 21/00
(52) U.S. Cl. ....................... 570/256; 570/101; 570/143; 570/144; 570/151; 570/190; 570/202
(58) Field of Search ................. 570/101, 143, 570/144, 151, 190, 202, 256

(56) References Cited

U.S. PATENT DOCUMENTS

| | | | |
|---|---|---|---|
| 3,780,123 A | 12/1973 | Suggitt | |
| 4,158,025 A | 6/1979 | Addison | |
| 4,238,346 A | 12/1980 | Sugahara et al. | |
| 4,409,413 A | 10/1983 | Iwayama et al. | |
| 4,935,561 A | * 6/1990 | Eichler et al. | ............... 570/202 |
| 5,175,135 A | 12/1992 | Lee et al. | |
| 5,223,236 A | 6/1993 | Inoue et al. | |
| 5,466,881 A | * 11/1995 | Pies et al. | ................... 570/202 |
| 6,060,417 A | 5/2000 | Kato et al. | |

* cited by examiner

Primary Examiner—Elvis O. Price
(74) Attorney, Agent, or Firm—Piper Rudnick LLP

(57) ABSTRACT

A catalyst composition with a high halogenated aromatics isomerization activity, a halogenated aromatic isomerization method using said catalyst composition, and a halogenated aromatics isomerization method capable of prolonging the life or regeneration period of the catalyst. The invention also includes a catalyst composition characterized in that the maximum diameter of secondary particles of the zeolite in the formed catalyst is 5 microns or less is used to improve the halogenated aromatics isomerization activity. Furthermore, if dissolved oxygen is decreased, the life or regeneration period of the catalyst can be prolonged.

5 Claims, 3 Drawing Sheets

METHOD FOR ISOMERIZING HALOGENATED AROMATICS

This application is a divisional of application Ser. No. 09/113,587, filed July 10, 1998 now abandoned, incorporated herein by reference.

BACKGROUND OF THE INVENTION

The present invention relates to a catalyst composition and a method for isomerizing halogenated aromatics. Particularly, the present invention relates to a catalyst and a method for isomerizing halogenated aromatics such as dichlorobenzene (DCB), chlorotoluene (CT) or dichlorotoluene (DCT), etc., for increasing m-DCB, m-CT, 2,6-DCT or 3,5-DCT.

DCB, one of halogenated aromatics, can be obtained by chlorinating benzene. However, since this reaction is strong in o-orientation and p-orientation, isomerization must be used when the m-isomer is necessary. Furthermore, the ratio of demand for respective DCB isomers is often different from the ratio of the respective isomers produced by chlorination. Therefore, also for effective utilization of DCB, a DCB isomerization method has an important technical significance.

When any one of respective DCB isomers or the m-DCB produced by isomerization is used alone, it must be separated.

Distillation as a method for separating isomers requires many rectifying columns since the respective isomers are close to each other in boiling point. Recently, Japanese Patent Publication (Tokko Hei) Nos. 1-12732 and 7-86092 disclose an adsorption separation method and a method of using adsorption separation and distillation in combination.

It is economically very important that the DCB isomers remaining after separating and removing the intended DCB isomer are re-used for isomerization reaction, to increase the concentration of the intended isomer. Subsequently the intended DCB isomer is separated and removed again, to repeat the cycle.

As a method for such isomerization reaction, Japanese Patent Publication (Tokko) No. 64-9972, etc. disclose a method of using acid type mordenite or a zeolite, the aperture of the largest pore of which comprises the 10-membered oxygen ring, as a catalyst. However, also for this method, it is industrially important to further improve isomerization activity.

CT can be obtained by chlorinating toluene. However, since this reaction is strong in o-orientation and p-orientation, isomerization must be used when the m-isomer is necessary. Furthermore, the ratio of demand for CT isomers is often different from the ratio of respective CT isomers produced by chlorination. Therefore, also for effective utilization of CT, a CT isomerization method has an important technical significance.

When any one of CT isomers or the m-CT produced by isomerization is used alone, it must be separated.

Distillation as a method for separating the isomers requires an ultraprecise rectifying column since the respective isomers are close to each other in boiling point, and cannot be said to be an industrial method. Recently, Japanese Patent Publication (Tokko) Nos. 63-24495 and 63-64412 disclose an adsorption separation method and a method of using adsorption separation and distillation in combination.

It is economically very important that the CT isomers remaining after separating and removing the intended CT isomer are subjected to isomerization reaction, to increase the concentration of the intended isomer again. Subsequently the intended CT isomer is separated and removed again, to repeat the cycle.

As a method for such isomerization reaction, Japanese Patent Publication (Tokko) No. 62-15050 discloses a method of using a zeolite, the aperture of the largest pore of which comprises the 10-membered oxygen ring, as a catalyst. However, also for this method, it is industrially important to further improve the isomerization activity.

Furthermore, in general, DCT is obtained by dichlorination of toluene. This reaction is a strongly oriented reaction, and the production ratio of the obtained isomers is 20 to 35% of 2,4-DCT: 25 to 55% of 2,5-DCT: 5 to 35% of 2,6-DCT: 8 to 12% of 2,3-DCT: 5 to 12% of 3,4-DCT. This reaction does not yield 3,5-DCT, and to obtain 3,5-DCT, DTC must be isomerized.

When any one of DCT isomers or 3,5-DCT produced by isomerization is used alone, it must be separated.

These isomers cannot be separated by distillation since they are close to each other in boiling point. So, for example, as disclosed in Japanese Patent Publication (Tokko) Nos. 1-45457 and 1-40016, the separation can be effected by an adsorption separation method or a method of using adsorption separation and distillation in combination.

It is very economically important that the DCT isomers remaining after separating and removing the intended DCT isomer are subjected to isomerization reaction again, to increase the concentration of the intended isomer. Subsequently the intended DCT isomer is separated and removed again, to repeat the cycle.

As a method for such isomerization reaction, Japanese Patent Publication (Tokko) Nos. 4-37054 and 37055 disclose a method of using a mordenite type zeolite (hereinafter called "mordenite"). However, also for this method, it is industrially important to further improve the isomerization activity.

If a zeolite-containing catalyst is used for isomerizing halogenated aromatics, the catalyst generally declines in performance with the lapse of time. So, the catalyst must be replaced by a new catalyst or regenerated by calcination, etc. at a proper time, and it is industrially very advantageous to prolong the life or regeneration period.

If these conventionally known isomerization catalysts can be further improved in activity, the reaction temperature can be lowered. If a catalyst is used for reaction, the catalytic activity declines, and it is generally practiced that to compensate the decline of activity, the reaction temperature is raised. Therefore, if the reaction temperature can be lowered, the catalyst can be used in a wider temperature range, and as a result, the catalyst life can be prolonged.

From the above points of view, the inventors studied intensively on the method for improving the catalytic activity, and as a result, found that if the maximum diameter of secondary particles of a zeolite in a formed catalyst is reduced, the catalytic activity in the reaction to isomerize halogenated aromatics can be improved, to achieve the present invention.

Furthermore, the inventors found that if the primary particle size of mordenite used as a zeolite for isomerizing DCT is reduced, the catalytic activity in the DCT isomerization reaction can be improved, to achieve the present invention.

Moreover, the inventors investigated the method for isomerizing halogenated aromatics, and as a result, found that if halogenated aromatics with a dissolved oxygen content of 15 wt ppm or less are used, the deactivation of the zeolite-containing catalyst can be inhibited, to prolong the life of the catalyst, for allowing efficient isomerization of halogenated aromatics.

OBJECTS OF THE INVENTION

An object of the present invention is to provide a catalyst composition with high halogenated aromatics isomerization activity.

Another object of the present invention is to provide a method for isomerizing halogenated aromatics, which can prolong the life or regeneration period of the catalyst.

Further other objects of the present invention will be clarified in the following description.

BRIEF DESCRIPTION OF THE INVENTION

The present invention achieves the above objects. The catalyst composition for isomerizing halogenated aromatics of the present invention is a catalyst composition for isomerizing halogenated aromatics, characterized in that the maximum diameter of secondary particles of the zeolite in the formed catalyst is 5 microns or less. The isomerizing catalyst composition of the present invention includes the following preferable embodiments.

(a) Said halogenated aromatics are compounds represented by the following general formula (I).

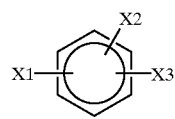

(I)

(where X1 stands for a halogen atom; X2, a hydrogen atom or halogen atom; and X3, a halogen atom or lower alkyl group).

(b) With a halogen atom selected as X1, a hydrogen atom as X2 and a halogen atom or methyl group as X3 in the general formula (I), the aperture of the largest pore of the zeolite comprises the 10-membered oxygen ring.

(c) Said halogenated aromatics are dichlorobenzene and chlorotoluene.

(d) With a halogen atom selected as X1, a halogen atom as X2, and a halogen atom or lower alkyl group with 1 to 4 carbon atoms as X3, or with a halogen atom selected as X1, a hydrogen atom as X2, and a lower alkyl group with 2 to 4 carbon atoms as X3 in the general formula (I), said zeolite is mordenite.

(e) Said halogenated aromatics are dichlorotoluene, trichlorobenzene are chloroethylbenzene.

(f) Said zeolite is an acid type zeolite.

(g) Mordenite of 0.2 micron or less in the longest axes of its primary particles is contained.

(h) The maximum diameter of secondary particles of mordenite in the formed catalyst containing said mordenite of 0.2 micron or less in the longest axes of its primary particles is 5 microns or less.

(i) Said catalyst composition contains rhenium.

(j) Said rhenium is contained by 0.05 to 2 wt % as metal based on the weight of the catalyst composition.

(k) Said catalyst composition contains rhenium and silver.

(l) Said rhenium is contained by 0.05 to 2 wt % as metal based on the weight of the catalyst composition, and said silver is contained by 0.5 to 10 wt % as metal based on the weight of the catalyst composition.

(m) Said rhenium is contained by 0.05 to 1 wt % as metal based on the weight of the catalyst composition, and said silver is contained by 1 to 7 wt % as metal based on the weight of the catalyst composition.

(n) Said catalyst composition further contains at least either of fluorine and phosphorus.

(o) Said at least either of fluorine and phosphorus is contained by 0.05 to 2 wt % as fluorine atoms and/or phosphorus atoms based on the weight of the catalyst composition.

(p) The silica/alumina molar ratio of the mordenite is 15 to 30.

Furthermore, the isomerization method of the present invention is a method for isomerizing halogenated aromatics, comprising the step of bringing the catalyst compound stated in any one of the above into contact with halogenated aromatics. The isomerization method of the present invention includes the following preferable embodiments.

(q) Halogenated aromatics with a dissolved oxygen content of 15 ppm or less are brought into contact with a zeolite-containing catalyst.

(r) Before the halogenated aromatics are brought into contact with the zeolite-containing catalyst, the halogenated aromatics are treated by dissipation treatment, reduced pressure treatment or distillation treatment, to remove the dissolved oxygen.

(s) Said zeolite-containing catalyst is the catalyst composition stated in any of the above.

DETAILED DESCRIPTION OF THE INVENTION

As the zeolite used in the present invention, any zeolite preferable for the halogenated aromatics to be isomerized is selected. In the present invention, it is preferable that the zeolite is of acid type.

The halogenated aromatics preferably used in the present invention include the compounds represented by the following general formula (I):

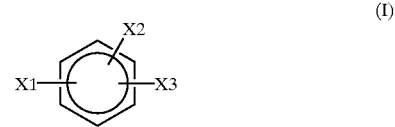

(I)

(where X1 stands for a halogen atom; X2, a hydrogen atom or halogen atom; and X3 a halogen atom or lower alkyl group; it is preferable that the lower alkyl group has 1 to 4 carbon atoms.)

In the present invention, when the halogenated aromatics are compounds with a halogen atom as X1, a hydrogen atom as X2 and a halogen atom or methyl group as X3 in the general formula (I) to have a relatively small molecular size, a zeolite, the aperture of the largest pore of which comprises the 10-membered oxygen ring, can be preferably used. Furthermore, when the halogenated aromatics are compounds with a halogen atom as X1, a halogen atom as X2 and a halogen atom or lower alkyl group with 1 to 4 carbon atoms as X3, or with a halogen atom as X1, a hydrogen atom as X2 and a lower alkyl group with 2 to 4 carbon atoms as X3 in the general formula (I) to have a relatively large molecular size, mordenite can be preferably used.

Halogenated aromatics with a halogen atom as X1, a halogen atom as X2 and a halogen atom or methyl group as X3 include chlorotoluene, bromotoluene, dichlorobenzene, dibromobenzene, chlorobromobenzene, etc. The present invention is effective for isomerizing especially chlorotoluene and dichlorobenzene.

Halogenated aromatics with a halogen atom as X1, a halogen atom as X2 and a halogen atom or lower alkyl group with 1 to 4 carbon atoms as X3 include dichlorotoluene, dibromotoluene, chlorobromotoluene, trichlorobenzene, tribromobenzene, dichloroethylbenzene, dibromoethylbenzene, etc. The present invention is effective for isomerizing especially dichlorotoluene and trichlorobenzene.

Halogenated aromatics with a halogen atom as X1, a hydrogen atom as X2 and a lower alkyl group with 2 to 4 carbon atoms as X3 include chloroethylbenzene, bromoethylbenzene, chloropropylbenzene, etc. The present invention is effective for isomerizing especially chloroethylbenzene.

Zeolites, the aperture of the largest pore of which comprises the 10-membered oxygen ring, are known as pentasil-type zeolites, and their compositions and production methods are stated in U.S. Pat. No. 3,894,106. The zeolites, the aperture of the largest pore of which comprises the 10-membered oxygen ring, include the ZSM-5 zeolite with its crystal structure stated in Nature 271, 30 March, 437 (1978) and the zeolites considered to belong to the same series. They include, for example, said ZSM-5, ZSM-8 stated in GB Patent No. 1334243, ZSM-11 stated in Japanese Patent Publication (Tokko) No. 53-23280, ZSM-21 stated in U.S. Pat. No. 4,001,346, ZSM-35 stated in Japanese Patent Laid-Open (Kokai) No. 53-144500, zeolite zeta 1 stated in Japanese Patent Laid-Open (Kokai) No. 51-67299, zeolite zeta 3 stated in Japanese Patent Laid-Open (Kokai) No. 51-67298, etc. Any zeolite, with a structure in which the aperture of the largest pore comprises the 10-membered oxygen ring, can of course be used, without being limited to those enumerated above.

Various methods for producing pentasil-type zeolites have been disclosed, for example, in Japanese Patent Laid-Open (Kokai) Nos. 52-115800, 53-134798 and 57-123815, etc.

It is preferable that the molar ratio of silica/alumina constituting such a zeolite is 10 to 100. A more preferable range is 18 to 50. If the silica/alumina molar ratio is less than 10 or more than 100, the catalytic activity tends to decline.

Mordenite is a zeolite which gives an X-ray diffraction pattern shown in Table 1 below.

| X-ray diffraction pattern of mordenite | | |
|---|---|---|
| Lattice spacing | d (Å) | Intensity |
| 13.6 | ± 0.2 | M |
| 10.2 | ± 0.2 | W |
| 9.0 | ± 0.2 | S |
| 6.56 | ± 0.1 | S |
| 6.40 | ± 0.1 | M |
| 6.05 | ± 0.1 | W |
| 5.80 | ± 0.1 | M |
| 4.52 | ± 0.08 | M |
| 3.99 | ± 0.08 | S |
| 3.83 | ± 0.08 | W |
| 3.76 | ± 0.08 | W |
| 3.53 | ± 0.05 | W |
| 3.46 | ± 0.05 | VS |
| 3.38 | ± 0.05 | S |
| 3.28 | ± 0.05 | W |
| 3.20 | ± 0.05 | S |
| 3.15 | ± 0.05 | W |

-continued

| X-ray diffraction pattern of mordenite | | |
|---|---|---|
| Lattice spacing | d (Å) | Intensity |
| 2.89 | ± 0.05 | M |
| 2.51 | ± 0.05 | W |

Mordenite includes a natural product and a synthetic product. In the present invention, the use of synthetic mordenite is preferable. Various methods for synthesizing mordenite are disclosed, for example, in Japanese Patent Publication (Tokko) No. 47-46677 and Japanese Patent Laid-Open (Kokai) Nos. 55-126529 and 58-91032, etc.

It is preferable that the molar ratio of silica/alumina constituting the mordenite structure is 15 to 30. If the silica/alumina molar ratio is less than 15 or more than 30, the catalytic activity tends to decline. Mordenite with a silica/alumina molar ratio of 15 to 30 can be obtained by acid extraction, etc. of mordenite for removing aluminum, or directly by synthesis. In the present invention, directly synthesized mordenite can be preferably used.

It is more preferable that the primary particle size of mordenite is 0.2 micron or less in longest axis.

As a general trend, the primary particle size of mordenite tends to be smaller if a nitrogen containing organic base such as tetraethylammonium hydroxide or a surfactant such as polyethylene glycol is present in the reaction mixture, though this cannot be generally said since the primary particle size is affected variously by the reaction mixture composition at the time of synthesis, crystallization temperature, crystallization time, stirring speed, etc. Furthermore, for the composition ratios in the reaction mixture, since the particle size complicatedly changes, depending on the silica and alumina contents and alkali concentration, it is preferable to select the optimum composition ratios. As for crystallization conditions, if the crystallization temperature is lower, or if the crystallization time is shorter, or if the stirring speed is higher, the primary particle size tends to be smaller. Irrespective of the method, in the present invention it is only required that mordenite is 0.2 micron or less in the longest axes of its primary particles.

The primary particle size of mordenite can be easily examined by a scanning electron microscope (SEM). It is preferable that the molar ratio of silica/alumina constituting the mordenite structure is 15 to 30. If the silica/alumina molar ratio is less than 15 or more than 30, the catalytic activity tends to decline.

When the zeolite is powdery, it must be formed for use as an industrial catalyst. It can be formed by various methods such as compression forming, kneading, oiling and dropping, but in the present invention, kneading can be preferably used. For kneading, a binder is generally necessary, and an inorganic oxide and/or clay is used as the binder. The binders which can be preferably used in the present invention include alumina sol and alumina gel. The amount of the binder is 5 to 30 parts by weight as absolute dry weight per 100 parts by weight of the zeolite. A preferable range is 10 to 20 parts by weight. If the formability is poor, it is effective to add an alkali metal salt or an alkaline earth metal salt such as sodium chloride, magnesium chloride or barium chloride or a surfactant such as polyvinyl alcohol, Span or Reodol for kneading. The particle size of the formed catalyst is very important since it greatly affects the diffusion velocity in the reaction to isomerize the halogenated aromatics. If the particle size is smaller, the diffusion velocity is faster preferably but the pressure loss becomes larger. So, a moderate particle size is preferable. A preferable particle size in the present invention is 0.05 to 2 mm. A more preferable range is 0.1 to 1 mm. The formed catalyst is then dried at 50 to 200-C, and subsequently calcined at 350 to 600-C, to be higher in strength.

The secondary particles of the zeolite used in the present invention are formed by aggregation of primary particles of the zeolite. The maximum diameter of secondary particles in the formed catalyst can be easily examined by a scanning electron microscope (SEM).

For the objects of the present invention, it is effective that the maximum diameter of secondary particles of the zeolite in the formed catalyst is 5 microns or less. When the raw zeolite is homogeneously mixed and formed with an inorganic oxide and/or clay, the secondary particles are partly broken and dispersed. If the secondary particles of the zeolite, in the formed catalyst are sufficiently small and are well dispersed, the effective catalytic reaction rate is higher, and a higher catalytic activity can be achieved in isomerization reaction. The maximum diameter of secondary particles in the formed catalyst can be controlled by forming conditions, the maximum diameter of secondary particles of the raw zeolite powder, etc. As forming conditions, the time for kneading the raw zeolite and an inorganic oxide and/or clay, water content, etc. are important. For example, if the kneading time is longer, the maximum diameter of secondary particles in the formed catalyst is preferably smaller. Furthermore, the maximum diameter of secondary particles of the raw zeolite powder can be controlled by the composition ratios of the reaction mixture at the time of synthesis, crystallization time, stirring conditions, drying method, etc. The synthesizing conditions must be selected properly since they depend on the raw material used and cannot be generally specified. According to the findings obtained so far, if the alkalinity in the reaction mixture at the time of synthesis is lower or if the crystallization time is shorter, the maximum diameter of secondary particles tends to be smaller.

In the present invention it is preferable that the zeolite contained in the formed catalyst is of acid type. If the zeolite is of acid type or ammonium ion type acting as a hydrogen ion precursor or organic cation type before forming, treatment for conversion into acid type is not necessarily required. However, if the zeolite contains alkali metal ions or alkaline earth metal ions, etc., ion exchange treatment for conversion into acid type is carried out. As ion exchange treatment, the zeolite can be directly converted into acid type using an aqueous solution of an inorganic acid or organic acid, etc., or the zeolite can be ion-exchanged to have ammonium ions introduced using an aqueous solution of ammonium chloride or ammonium nitrate, etc. and calcined to be converted into acid type. Since ion exchange by an acid aqueous solution is likely to remove aluminum from the zeolite, ion exchange by an ammonium salt aqueous solution is preferable. The catalyst composition prepared like this is dried at 50 to 200-C and subsequently calcined at 350 to 600-C, to be used in the reaction for isomerizing halogenated aromatics.

In the isomerization of CT or DCB, the presence of an aromatic hydrocarbon or any other halogenated aromatics is effective for inhibiting side reactions and prolonging the catalyst life.

For isomerizing DCT, TCB or CEB, etc., it is preferable to load rhenium with hydrogenation activity on the catalyst or to introduce silver ions into mordenite, for more effective functioning of the catalyst. It can happen that silver ions cause reduction or are formed into another compound during reaction, but this does not pose any problem in catalytic performance. It is also preferable to add fluorine and/or phosphorus to the catalyst. When the catalyst is used for reaction, it is preferable that DCT as a raw material supplied is brought into contact with the catalyst, in liquid phase. It is also preferable that hydrogen is present with the raw material supplied, since the decline of catalytic activity can be inhibited. If hydrogen is dissolved in the DCT liquid phase, a higher effect can be manifested. To dissolve an effective amount of hydrogen into DCT, it is preferable that the reaction pressure is 4 MPa or more.

The introduction of silver ions into mordenite can be easily achieved by ion-exchanging the formed mordenite catalyst, for example, by a silver nitrate aqueous solution. It is preferable that the amount of silver ions introduced is 0.5 to 10 wt % as metal based on the weight of the catalyst composition. A more preferable range is 1 to 7 wt %. A catalyst composition containing silver ions is effective for inhibiting side reactions in the DCT isomerization reaction. The silver ions introduced into mordenite can be converted into the metal or any other compound such as chloride during reaction, but this does not lower the catalytic performance.

Especially when rhenium is loaded with the catalyst for isomerization reaction in the presence of hydrogen with DCT as liquid phase, rhenium functions as a hydrogen activating component and removes the high boiling point compounds which cover the active sites of the catalyst and poison the catalytic performance, thereby effectively maintaining the catalytic activity. The rhenium compounds which can be used here include perrhenic acid, ammonium perrhenate, rhenium chloride, etc. It is preferable that the amount of rhenium carried is 0.05 to 2 wt % as metal based on the weight of the catalyst composition. A more preferable range is 0.05 to 1 wt %.

The catalyst composition produced like this is dried at 50 to 200-C and subsequently calcined at 350 to 600-C, to be used for DCT isomerization reaction.

It is also effective for DCT isomerization that at least either of fluorine and phosphorus is introduced into the catalyst composition.

At least either of fluorine and phosphorus can be introduced into the catalyst composition by impregnation or mixing, etc. Preferable fluorine compounds which can be used here include water soluble fluorine compounds such as ammonium fluoride. Preferable phosphorus compounds which can be used here include water soluble phosphorus compounds such as phosphoric acid, ammonium phosphate and ammonium hydrogenphosphate. It is preferable that fluorine and/or phosphorus is contained by 0.05 to 2 wt % as fluorine atoms and/or phosphorus atoms based on the weight of the catalyst composition.

The catalyst composition produced like this is dried at 50 to 200° C. and subsequently calcined at 350 to 600° C., to be used in the reaction to isomerize halogenated aromatics.

For the reaction to isomerize halogenated aromatics, any of fixed bed, moving bed and fluidized bed can be used. In view of easy operation, fixed bed flow reaction is especially preferable. It is preferable that the reaction temperature is 250 to 500° C. A more preferable range is 250 to 350° C. The reaction can take place in either of vapor phase or liquid phase, but if any high boiling point compound is byproduced, liquid phase reaction is preferable. Furthermore, water can be removed as stated in Japanese Patent Publication (Tokko) No. 4-46933, or a diluent stated in Japanese Patent Publication (Tokko) No. 62-15051 can also be added.

In the reaction to isomerize DCT, CEB or TCB, etc., it is preferable that the halogenated aromatics in liquid phase are brought into contact with the catalyst in the presence of hydrogen. The reaction with the halogenated aromatics in liquid phase causes both the high boiling point compounds and the reaction product respectively produced in the reaction to flow out of the system, without covering the active sites of the catalyst, thus inhibiting the deactivation of the catalyst with the lapse of time. It can be considered that hydrogen can hydrocrack the high boiling point compounds covering the active sites of the catalyst, for removing them, and as a result, that the deactivation of catalytic activity is inhibited. It is preferable that the amount of hydrogen is 0.005 to 0.2 as a molar ratio to DCT. A more preferable range is 0.02 to 0.2. In this case, it is especially preferable that hydrogen is dissolved in DCT for manifesting a higher effect. For dissolving hydrogen into the liquid phase DCT, it is preferable that the reaction pressure is 4 MPa or more, since the deactivation of catalytic activity can be prevented.

The weight space velocity (WHSV) is 0.05 to 10 $Hr^{-1}$. A preferable range is 0.1 to 5 $Hr^{-1}$.

In the present invention, if the dissolved oxygen content of the halogenated aromatics is kept at 15 wt ppm or less, the deactivation of the catalyst can be prevented. It is preferable that the dissolved oxygen content is as small as 5 wt ppm or less. More preferable is 1 wt ppm or less.

The dissolved oxygen content of halogenated aromatics can be measured using a Beckmann dissolved oxygen meter or polarographic dissolved oxygen meter, etc.

The dissolved oxygen content of halogenated aromatics can be kept at 15 wt ppm or less by dissipation treatment, reduced pressure treatment or distillation treatment, etc.

In the present invention, the dissipation treatment means to bring halogenated aromatics liquid containing dissolved oxygen into contact with an inert gas such as $N_2$ for removing the dissolved oxygen from the halogenated aromatics. For dissipation, for example, $N_2$ can be directly blown into halogenated aromatics liquid in a storage tank for bubbling, or halogenated aromatics and $N_2$ are brought into mutual contact in counter current in a plate column or packed column, etc. The operating pressure can be any of atmospheric pressure, pressurization or reduced pressure. The operating temperature is usually lower than the temperature at which the halogenated aromatics can be kept in liquid phase.

As reduced pressure treatment, for example, a storage tank which contains halogenated aromatics containing dissolved oxygen is reduced in pressure by a vacuum pump, etc., or halogenated aromatics liquid is treated by reduced pressure in a plate column or packed column, etc. for expelling dissolved oxygen. The operating pressure can be vacuum or atmospheric pressure, but a lower pressure is preferable. The operating temperature is usually lower than the temperature at which the halogenated aromatics can be kept in liquid phase.

Distillation treatment can be executed according to a conventional method. The distillation column can be a plate column or packed column, etc., and the operating pressure can be any of atmospheric pressure, pressurization or reduced pressure.

The dissolved oxygen, if contained in the halogenated aromatics, reacts with the halogenated aromatics in the isomerization reaction, to produce an oxygen-containing compound, increasing the molecular weight and covering the active sites of the catalyst, thereby lowering the catalytic activity. Therefore, it can be considered that if the dissolved oxygen is decreased, the decrease of active sites can be prevented, allowing the catalyst regeneration period to be prolonged.

For the isomerization reaction, any of fixed bed, moving bed and fluidized bed can be used, and either flow method or batch method can be adopted.

According to the present invention, the catalytic activity in the reaction to isomerize halogenated aromatics can be improved, and the reaction temperature can be lowered. In addition, by decreasing dissolved oxygen, the life or regeneration period of the catalyst can be prolonged.

EXAMPLES

Figure 1:
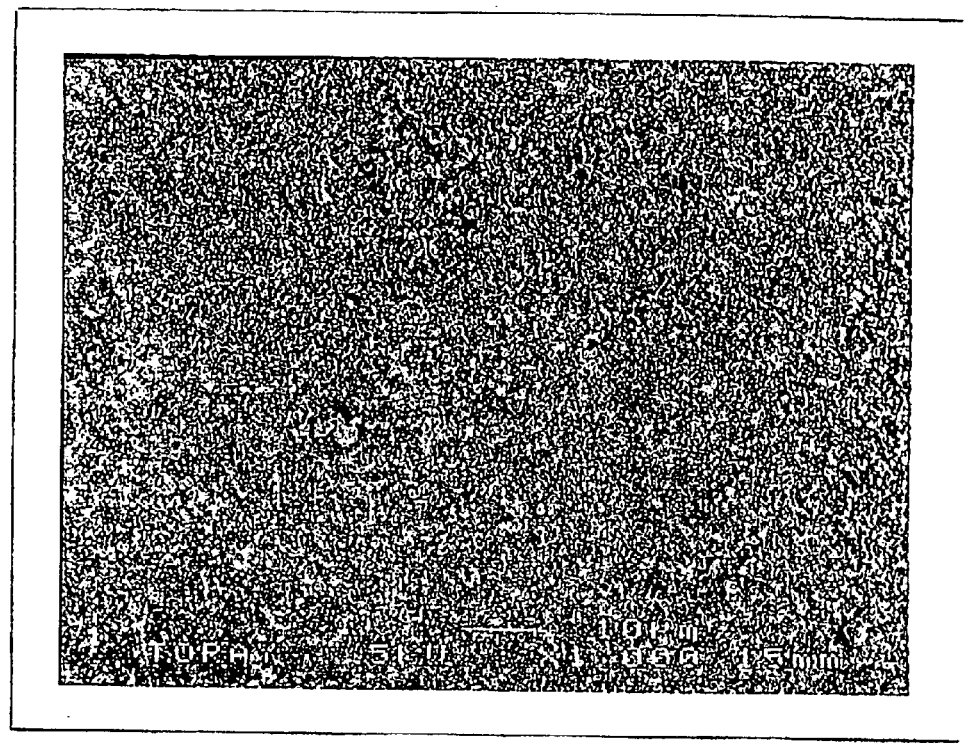
FIG. 1 is a diagram showing an SEM image of the catalyst compound A produced in Example 2.

The invention will be described in more detail with reference to the following examples, which are not intended to restrict the scope of the invention.

Example 1

Synthesis of Pentasil-Type Zeolite

An aqueous solution was prepared by dissolving in 583.8 g of water, 7.3 of solid caustic soda (containing 96.0 wt % NaOH and 4.0 wt % $H_2O$, from Katayama Kagaku) and 10.2 g of tartaric acid powder (containing 99.7 wt % tartaric acid and 0.3 wt % $H_2O$, from Katayama Kagaku). To this aqueous solution was added 35.4 g of sodium aluminate solution (containing 18.5 wt % $Al_2O_3$, 26.1 wt % NaOH and 55.4 wt % $H_2O$, from Sumitomo Chemical). To the resulting homogenous solution was slowly added with stirring 111.5 g of silicic acid powder (containing 91.6 wt % $SiO_2$, 0.33 wt % $Al_2O_3$ and 0.27 wt % NaOH, "Nipseal VN-3" from Nippon Silica). There was obtained a homogenous aqueous slurry having the following composition (in molar ratio).

| | | |
|---|---|---|
| $SiO_2/Al_2O_3$ | 25 | |
| $H_2O/SiO_2$ | 20 | |
| $OH^{-1}/SiO_2$ | 0.164 | |
| $A/Al_2O_3$ | 1.0 | A: tartrate |

The slurry was heated at 160° C. for 72 hours with stirring (250 rpm) in a 1-liter autoclave. The reaction product was washed with distilled water and filtered five times and then dried overnight at about 120-C. Thus there was obtained a pentasil-type zeolite which gives an X-ray diffraction pattern shown in Table 2 below and has the silica/alumina molar ratio of 21.9.

| X-ray diffraction pattern of pentasil-type zeolite | | |
|---|---|---|
| Lattice spacing | d (Å) | Intensity |
| 11.2 | ± 0.2 | VS |
| 10.1 | ± 0.2 | S |
| 9.8 | ± 0.2 | M |
| 6.37 | ± 0.1 | W |
| 6.00 | ± 0.1 | W |
| 5.71 | ± 0.1 | W |
| 5.58 | ± 0.1 | W |
| 4.37 | ± 0.08 | W |
| 4.27 | ± 0.08 | W |
| 3.86 | ± 0.08 | VS |
| 3.82 | ± 0.08 | VS |
| 3.75 | ± 0.08 | S |
| 3.72 | ± 0.08 | S |
| 3.66 | ± 0.05 | M |
| 3.00 | ± 0.05 | M |
| 2.00 | ± 0.05 | W |

Example 2

Preparation of Catalyst: Catalyst Composition A

The formed pellet (30 g dry base) was treated with 10 wt % aqueous solution of ammonium chloride at 80–85° C. for 1 hour. The ion-exchange treatment was repeated 5 times in the same manner as above. The treatment was followed by rinsing with distilled water 5 times. It was dried overnight at 120° C., to obtain an ammonium ion-exchanged formed pellet. Then, it was calcined at 550° C. for 2 hours, to convert ammonium ions into hydrogen ions. Thus, there was obtained a catalyst compound A, which contained an acid type zeolite, the aperture of the largest pore of which comprised the 10-membered oxygen ring. SEM observation shows that the maximum diameter of secondary particles of the zeolite in the catalyst was 3 microns. An observed SEM image is shown in FIG. 1.

Comparative Example 1

Preparation of Catalyst: Catalyst Composition B

Figure 2:
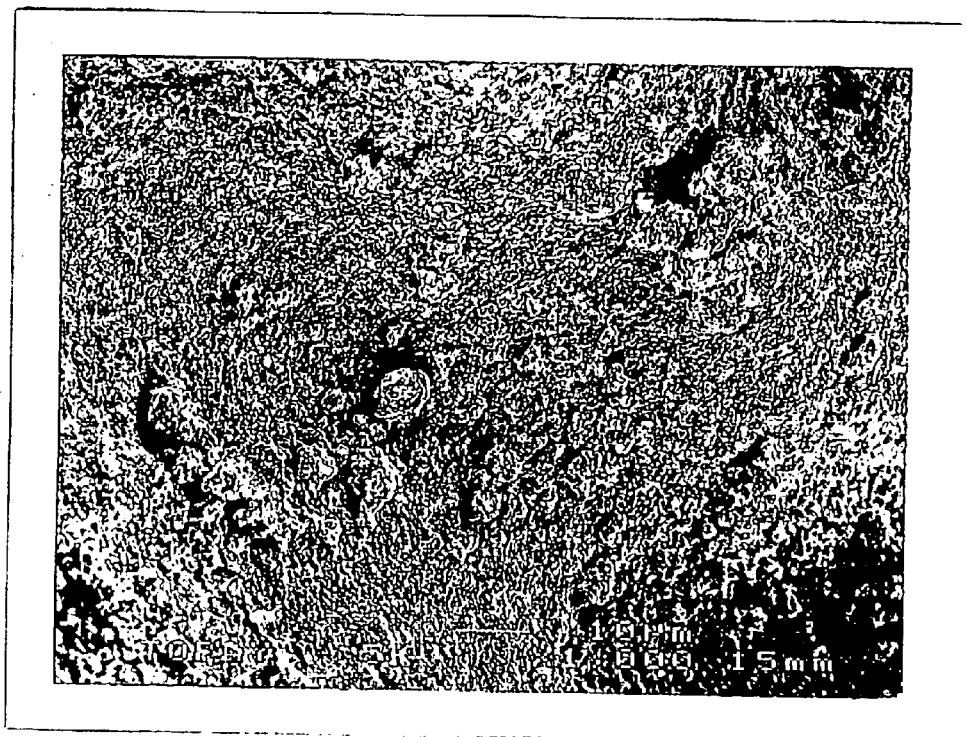
FIG. 2 is a diagram showing an SEM image of the catalyst compound B produced in Comparative Example 1.

A catalyst composition B was obtained as described for preparing the catalyst composition A of Example 2, except that the kneading time for catalyst forming was about 30 minutes. SEM observation shows that the maximum diameter of secondary particles of the zeolite in the formed catalyst was 10 microns. An observed SEM image is shown in FIG. 2.

Example 3

CT Isomerization Reaction

The catalyst composition A (Example 2) and the catalyst composition B (Comparative Example 1) obtained by the above method and different in the maximum diameter of secondary particles of the zeolite, the aperture of the largest pore of which comprised the 10-membered oxygen ring, in the formed catalyst were used for CT isomerization reaction tests in liquid phase. The results are shown in Table 3 below.

Evaluation of catalytic performance (CT isomerization reaction)

| Catalyst | A (Example 2) | B (Comparative Example 1) |
|---|---|---|
| Reaction conditions | | |
| Reaction temperature ° C. | 260 | 260 |
| Reaction pressure MPa-G | 3.4 | 3.4 |
| WHSV Hr | 1.5 | 1.5 |
| Reaction time Hrs | 202 | 206 |
| Supplied raw material | | |
| o-CT/benzene wt/wt | 2/1 | 2/1 |
| o-CT isomerization rate wt% | 51.2 | 45.6 |
| CT isomer ratio wt% | | |
| o-CT/CT | 48.8 | 54.4 |
| m-CT/CT | 37.6 | 33.1 |
| p-CT/CT | 13.6 | 12.5 |

From Table 3, it can be seen that if the maximum diameter of secondary particles of the zeolite, the aperture of the largest pore of which comprises the 10-membered oxygen ring, in the formed catalyst is smaller than 5 microns, the catalytic activity is higher and the reaction temperature can be lowered.

Example 4

DCB Isomerization Reaction

The catalyst composition A (Example 2) and the catalyst composition B (Comparative Example 1) obtained by the above method and different in the maximum diameter of secondary particles of the zeolite, the aperture of the largest pore of which comprised the 10-membered oxygen ring, in the formed catalyst were used for o-DCB isomerization reaction tests. The results are shown in Table 4 below.

Evaluation of catalytic performance (DCB isomerization reaction)

| Catalyst | A (Example 2) | B (Comparative Example 1) |
|---|---|---|
| Reaction conditions | | |
| Reaction temperature ° C. | 350 | 350 |
| Reaction pressure MPa-G | 2.9 | 2.9 |
| WHSV Hr | 4.0 | 4.0 |
| Reaction time Hrs | 24 | 24 |
| o-DCB conversion percentage wt% | 68.2 | 57.9 |
| Reaction product wt% | | |
| CB | 0.01 | 0.02 |
| o-DCB | 31.77 | 42.13 |
| m-DCB | 46.50 | 41.43 |
| p-DCB | 21.72 | 16.42 |
| ΣDCB | 99.99 | 99.98 |

Note: CB = Chlorobenzene

From Table 4, it can be seen that if the maximum diameter of secondary particles of the zeolite, the aperture of the largest pore of which comprises the 10-membered oxygen ring, in the formed catalyst is smaller than 5 microns, the catalytic activity is higher and the reaction temperature can be lowered.

Example 5

Influence of Dissolved Oxygen

The raw material obtained by nitrogen bubbling of o-DCB for removing oxygen (dissolved oxygen content nearly 0 ppm, measured by a polarographic dissolved oxygen meter) was treated to be dehydrated by a molecular sieve, and brought into contact with the catalyst composition A, for a liquid phase isomerization reaction test. The reaction conditions are shown in Table 5 below.

| | |
|---|---|
| Reaction temperature ° C. | 324 |
| Reaction pressure MPa-G | 3.9 |
| WHSV $Hr^{-1}$ | 0.4 |

Figure 3:
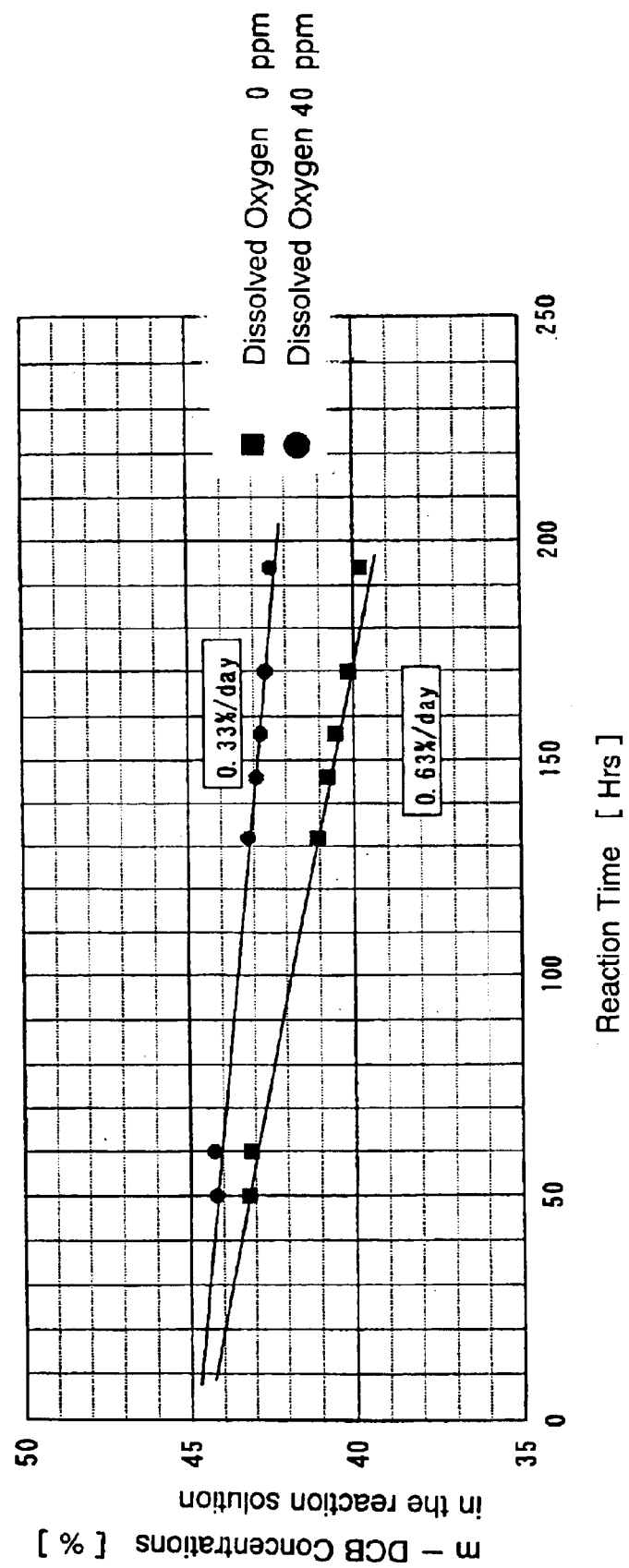
FIG. 3 is a diagram showing the reaction times and m-DCB concentrations in the reaction solutions in Example 5 and Comparative Example 2.

The degradation rate of the catalyst is expressed by the m-DCB content decrease rate in the DC isomer mixture used as the reaction solution. The catalyst deactivation rate in this example is shown in FIG. 3 and Table 6.

Comparative Example 2

An isomerization reaction test was carried out as described in Example 5, except that o-DCB saturated with air (dissolved oxygen content about 40 ppm, measured by a polarographic dissolved oxygen meter) was used as the raw material. The results are shown in FIG. 3 and Table 6 below.

| | Dissolved oxygen content of raw material | Catalyst degradation rate |
|---|---|---|
| Example 5 | 0 ppm | 0.33%/day |
| Comparative Example 2 | Approx. 40 ppm | 0.63%/day |

Example 6

Synthesis of Mordenite 1

A homogeneous aqueous solution was prepared by dissolving in 567 g of distilled water, 0.40 g of solid caustic soda (containing 96.0 wt % of NaOH and 4.0 wt % of $H_2O$, from Katayama Kagaku), 23.89 g of sodium aluminate solution (containing 18.5 wt % of $Al_2O_3$, 26.1 wt % of NaOH and 55.4 wt % of $H_2O$, from Sumitomo Chemical) and 55.2 g of tetraethylammonium hydroxide (hereinafter called TEAOH) (containing 20 wt % of TEAOH and 80 wt % of $H_2O$, from Sanyo Chemical). To this aqueous solution was slowly added with stirring 65.5 g of hydrous silicic acid (containing 91.6 wt % of $SiO_2$, 0.33 wt % of $Al_2O_3$ and 0.27 wt % of NaOH, Nipseal VN-3, from Nippon Silica) was gradually added with stirring. There was obtained a homogeneous aqueous slurry having the following slurry (in molar ratio).

| | |
|---|---|
| $SiO_2/Al_2O_3$ | 22 |
| $OH^{-1}/SiO_2$ | 0.245 |
| $TEA/SiO_2$ | 0.075 |
| $H_2O/SiO_2$ | 35 |

The slurry was heated at 160-C for 7 days with stirring (250 rpm) in a 1000 ml autoclave. The reaction product was washed with distilled water and filtered five times and then dried overnight at about 120° C. Thus there was obtained mordenite which gives an X-ray diffraction pattern shown in Table 1 and has the silica/alumina molar ratio of 18.5. The primary particles of the mordenite observed by SEM were 0.12 micron in the longest axis.

Example 7

Synthesis of Mordenite 2

A homogeneous aqueous solution was prepared by dissolving in 575 g of distilled water, 0.53 g of solid caustic soda (containing 96.0 wt % of NaOH and 4.0 wt % of $H_2O$, from Katayama Kagaku), 25.0 g of sodium aluminate solution (containing 18.5 wt % of $Al_2O_3$, 26.1 wt % of NaOH and 55.4 wt % of $H_2O$, from Sumitomo Chemical) and 66.6 g of TEAOH (containing 20 wt % of TEAOH and 80 wt % of $H_2O$, from Sanyo Chemical). To the homogeneous solution was added slowly with stirring 78.7 g of hydrous silicic acid (containing 91.6 wt % of $SiO_2$, 0.33 wt % of $Al_2O_3$ and 0.27 wt % of NaOH, Nipseal VN-3, from Nippon Silica). There was obtained a homogeneous aqueous slurry having the following composition (in molar ratio).

| | |
|---|---|
| $SiO_2/Al_2O_3$ | 25 |
| $OH^{-1}/SiO_2$ | 0.246 |
| $TEA/SiO_2$ | 0.075 |
| $H_2O/SiO_2$ | 30 |

The slurry was heated at 160-C for 7 days with stirring (250 rpm) in an autoclave. The reaction product was washed with distilled water and filtered five times and then dried overnight at about 120° C. Thus there was obtained mordenite which gives an X-ray diffraction pattern shown in Table 1 and has the silica/alumina molar ratio of 21.5. The primary particles of the mordenite observed by SEM were 0.16 micron in the longest axis.

Example 8

Synthesis of Mordenite 3

An aqueous solution was prepared by dissolving in 587 g of distilled water, 21.3 g of solid caustic soda (containing 96.0 wt % of NaOH and 4.0 wt % of $H_2O$, from Katayama Kagaku) and 21.3 g of tartaric acid powder (containing 99.7 wt % of tartaric acid and 0.3 wt % of $H_2O$, from Katayama Kagaku). To the solution was added 29.2 g of sodium aluminate solution (containing 18.5 wt % of $Al_2O_3$, 26.1 wt % of NaOH and 55.4 wt % of $H_2O$, from Sumitomo Chemical) was added. There was obtained a homogeneous solution, to which was added slowly with stirring 111.5 g of hydrous silicic acid (containing 91.6 wt % of $SiO_2$, 0.33 wt % of $Al_2O_3$ and 0.27 wt % of NaOH, Nipseal VN-3, from Nippon Silica). There was obtained a homogeneous aqueous slurry having the following composition (in molar ratio).

| | | |
|---|---|---|
| $OH^{-1}/SiO_2$ | 0.25 | |
| $H_2O/SiO_2$ | 20 | |
| $T/Al_2O_3$ | 2.5 | T: tartrate |

The slurry was heated at 160° C. for 3 days with stirring (250 rpm) in a 1000 ml autoclave. The reaction product was washed with water and filtered five times and then dried overnight at about 120° C. Thus there was obtained mordenite which gives an X-ray diffraction pattern shown in Table 1 and has the silica/alumina molar ratio of 18.6. The primary particles of the mordenite observed by SEM were 0.36 micron in the longest axis.

Example 9

Synthesis of Mordenite 4

A homogeneous aqueous solution was prepared by dissolving in 562 g of distilled water, 42.6 g of sodium aluminate solution (containing 18.5 wt % of $Al_2O_3$, 26.1 wt % of NaOH and 55.4 wt % of $H_2O$, from Sumitomo Chemical) and 69.9 g of TEAOH (containing 20 wt % of TEAOH and 80 wt % of $H_2O$, from Sanyo Chemical). To this aqueous solution was added slowly with stirring 78.7 g of hydrous silicic acid (containing 91.6 wt % of $SiO^2$, 0.33 wt % of $Al_2O_3$ and 0.27 wt % of NaOH, Nipseal VN-3, from Nippon Silica). There was obtained a homogeneous aqueous slurry having the composition (in molar ratio).

| | |
|---|---|
| $SiO_2/Al_2O_3$ | 15 |
| $OH^{-1}/SiO_2$ | 0.315 |
| $TEA/SiO_2$ | 0.079 |
| $H_2O/SiO_2$ | 30 |

The slurry was heated at 160° C. for 7 days with stirring (250 rpm) in a 1000 ml autoclave. The reaction product was washed with distilled water and filtered five times and then dried overnight at about 120° C. Thus there was obtained mordenite which gives an X-ray diffraction pattern shown in Table 1 and has the silica/alumina ratio of 13.1. The primary particles of the mordenite observed by SEM were 0.11 micron in the longest axis.

Example 10

Preparation of Catalysts: Catalyst Compositions C and D

A mixture was obtained by adding 4 g of alumina powder (containing 75.0 wt % of $Al_2O_3$, SCF type, from Condia) with boehmite structure (a-alumina monohydrate), 15 g of alumina sol (containing 10 wt % of $Al_2O_3$, Colloidal Alumina 200, from Nissan Chemical) and 4.3 g of alumina gel (containing 70 wt % of $Al_2O_3$, Cataloid AP (C-10), from Shokubai Kasei) to 30 g (absolute dry weight) of the mordenite powder obtained in Example 6, and was kneaded for about 2 hours. During kneading, a proper amount of distilled water was added, while the kneaded state was observed. There was obtained a pasty mixture, which was formed into pellets like noodles through a screen with 0.3 mm dia. holes. The product was dried overnight at 120° C. and then calcined at 500° C. for 2 hours.

The formed pellet (30 g dry base) was treated with 10 wt % aqueous solution of ammonium chloride at 80–85° C. for 1 hour. The ion-exchange treatment was repeated 5 times in the same manner as above. The treatment was followed by rinsing with distilled water 5 times. It was dried overnight at 120° C., to obtain an ammonium ion-exchanged formed pellet.

Figure 4:
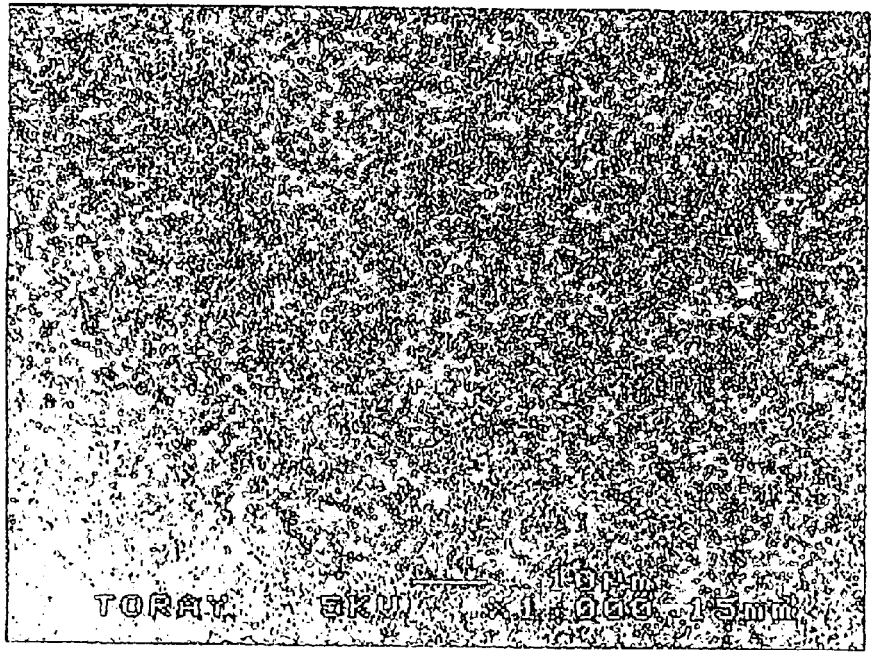
FIG. 4 is a diagram showing an SEM image of the catalyst compound C produced in Example 10.

One half of the ammonium ion-exchanged formed pellet was immersed in 30 g of an aqueous solution containing 75 mg, as rhenium metal, of perrhenic acid, at room temperature for 3 hours. Then, the immersed pellet was filtlated, dried overnight at 120° C. and calcined at 500° C. for 1 hour and in succession at 540° C. for 3 hours, to convert ammonium ions into hydrogen ions, for obtaining a catalyst composition C containing acid type mordenite. The catalyst composition C contained 0.3 wt % of rhenium. SEM observation shows that the maximum diameter of secondary particles of the mordenite in the formed catalyst was 3 microns. An SEM image observed is shown in FIG. 4.

On the other hand, the remaining half of the obtained ammonium ion-exchanged formed pellet was treated with 30 g of an aqueous solution containing 0.45 g, as silver metal, of silver nitrate at room temperature for 30 minutes and in succession at 70° C. for 1 hour. The ion exchange treatment was followed by rinsing with distilled water 5 times. It was dried overnight at 120° C., immersed in 30 g of an aqueous solution containing 75 mg, as rhenium metal, of perrhenic acid at room temperature for 3 hours. The immersed pellet was drained, dried overnight at 120° C. and calcined at 500° C. for 1 hour and in succession at 540° C. for 3 hours, to convert ammonium ions into hydrogen ions, for obtaining a catalyst composition D containing acid type mordenite. The catalyst composition D contained 2.8 wt % of silver and 0.3 wt % of rhenium. SEM observation shows that the maximum diameter of secondary particles of the mordenite in the formed catalyst was 3 microns.

Example 11

Preparation of Catalysts: Catalyst Compositions E and F

A mixture was obtained by adding 4 g of alumina powder (containing 75.0 wt % of $Al_2O_3$, SCF type, from Condia) with boehmite structure (a-alumina monohydrate), 15 g of alumina sol (containing 10 wt % of $Al_2O_3$, Colloidal Alumina 200, from Nissan Chemical) and 4.3 g of alumina gel (containing 70 wt % of $Al_2O_3$, Cataloid AP (C-10), from Shokubai Kasei) to 30 g (absolute dry weight) of the mordenite powder obtained in Example 7, and was kneaded for about 2 hours. During kneading, a proper amount of distilled water was added while the kneaded state was observed, to obtain a pasty mixture. It was formed into a pellet like noodles through a screen with 0.3 mm dia. holes. The formed pellet was dried overnight at 120-C and then calcined at 500° C. for 2 hours.

The formed pellet (30 g dry base) was treated with 10 wt % aqueous solution of ammonium chloride at 80–85-C for 1 hour. The ion-exchange treatment was repeated 5 times in the same manner as above. The treatment was followed by rinsing with distilled water 5 times. It was dried overnight at 120° C. to obtain an ammonium ion-exchanged formed pellet.

One half of the ammonium ion-exchanged formed pellet was immersed in 45 g of 1N ammonium fluoride aqueous solution at room temperature for 3 hours, and the immersed pellet was drained and immersed in 30 g of an aqueous solution containing 75 mg, as rhenium metal, of perrhenic acid at room temperature for 3 hours. The immersed pellet was drained, dried overnight at 120° C. and calcined at 500° C. for 1 hour and in succession at 540° C. for 3 hours, to convert ammonium ions into hydrogen ions, for obtaining a catalyst composition E containing acid type mordenite. The catalyst composition E contained 0.3 wt % of rhenium and 0.9 wt % of fluorine. SEM observation shows that the maximum diameter of secondary particles of the mordenite in the formed catalyst was 3 microns.

On the other hand, the remaining half of the ammonium ion-exchanged formed pellet was treated with 30 g of an aqueous solution containing 0.45 g, as silver metal, of silver nitrate at room temperature for 30 minutes and in succession at 70° C. for 1 hour. The ion-exchange treatment was followed by rinsing with distilled water 5 times. It was dried overnight at 120° C., and immersed in 45 g of 1N ammonium fluoride aqueous solution at room temperature for 3 hours. Then, the immersed pellet was drained and immersed in 30 g of an aqueous solution containing 75 mg, as rhenium metal, of perrhenic acid at room temperature for 3 hours. The immersed pellet was then drained, dried overnight at 120° C. and calcined at 500° C. for 1 hour and in succession at 540° C. for 3 hours, to convert ammonium ions into hydrogen ions, for obtaining a catalyst composition F containing acid type mordenite. The catalyst composition F contained 2.8 wt % of silver, 0.3 wt % of rhenium and 0.9 wt % of fluorine. SEM observation shows that the maximum diameter of secondary particles of the mordenite in the formed catalyst was 3 microns.

Example 12

Preparation of Catalyst: Catalyst Composition G

A catalyst composition G was obtained using the mordenite powder obtained in Example 8, as described for preparing the catalyst composition C of Example 10. SEM observation shows that the maximum diameter of secondary particles of the mordenite in the formed catalyst was 4 microns.

Example 13

Preparation of Catalyst: Catalyst Composition H

A catalyst composition H was obtained using the mordenite powder obtained in Example 9, as described for preparing the catalyst composition F of Example 11. SEM observation shows that the maximum diameter of secondary particles of the mordenite in the formed catalyst was 4 microns.

Comparative Example 3

Preparation of Catalyst: Catalyst Composition 1

Figure 5:
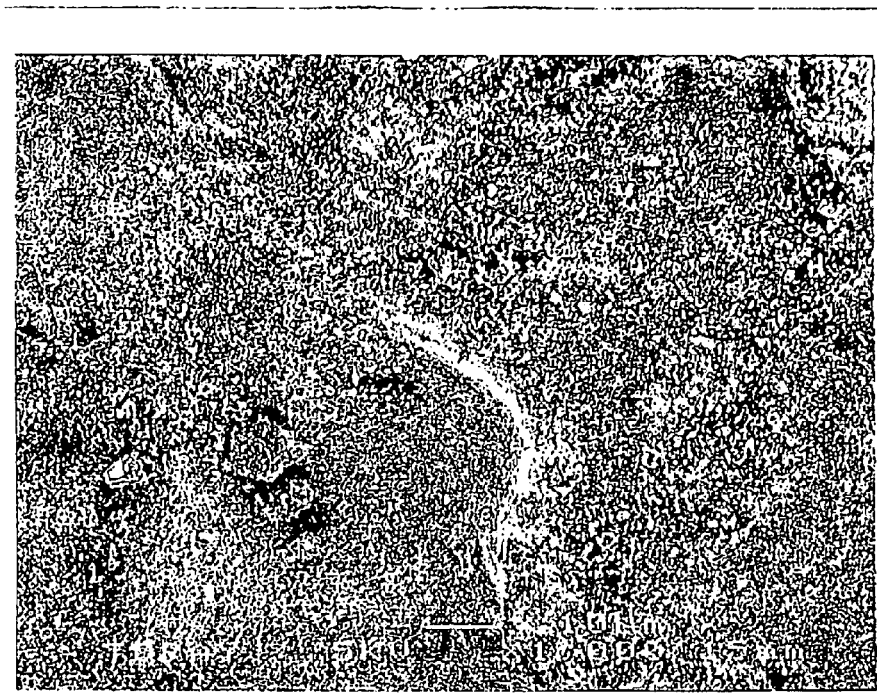
FIG. 5 is a diagram showing an SEM image of the catalyst compound I produced in Comparative Example 3.
Figure 3:
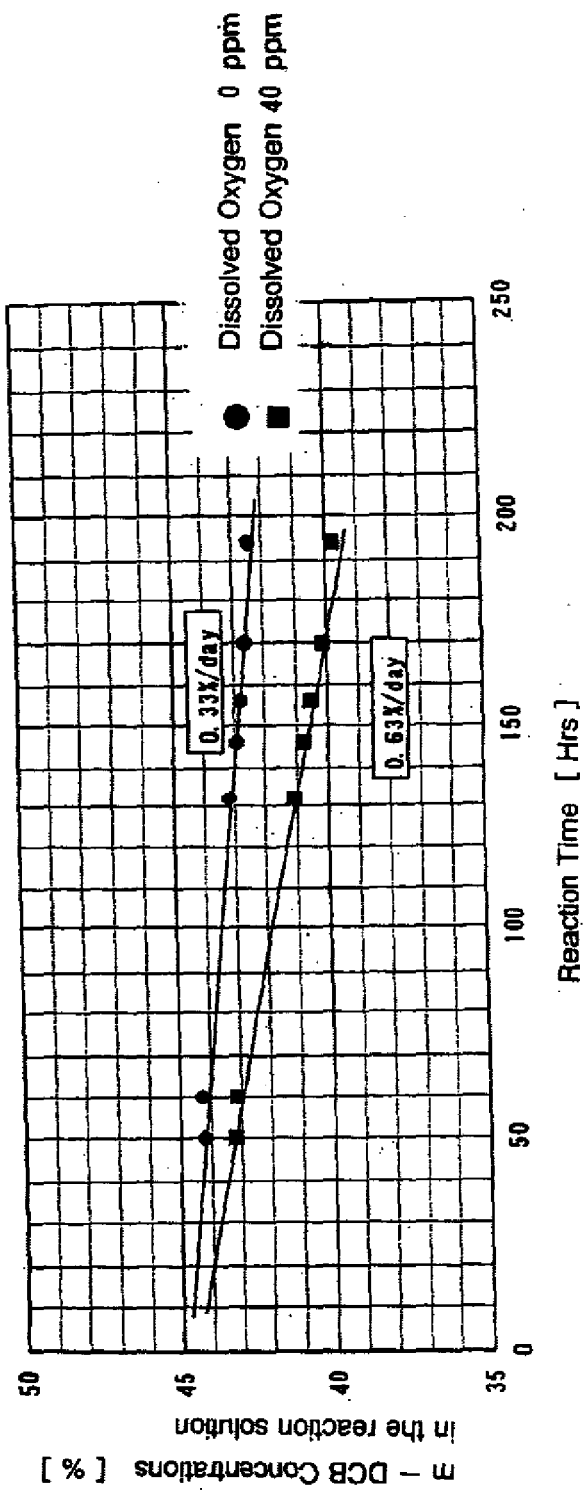

A catalyst composition I was obtained as described for preparing the catalyst composition F of Example 11, except that the kneading time for catalyst forming was about 30 minutes. SEM observation shows that the maximum diameter of secondary particles of the mordenite in the formed catalyst was 10 microns. An SEM image observed is shown in FIG. 5.

Example 14

DCT Isomerization Reaction

Seven catalyst compositions C (Example 10) through I (Comparative Example 3) prepared as described above were tested in DCT isomerization reaction. The results are shown in Table 7 below.

| Catalyst | Supplied raw material | C (Example 10) | D (Example 10) | E (Example 11) | F (Example 11) | G (Example 12) | H (Example 13) | I (Comparative Example 3) |
|---|---|---|---|---|---|---|---|---|
| Reaction conditions | | | | | | | | |
| Reaction temperature °C. | | 320 | 320 | 320 | 320 | 335 | 330 | 345 |
| Reaction pressure MPa-G | | 8.9 | 8.9 | 8.9 | 8.9 | 8.9 | 8.9 | 8.9 |
| H/DCT mole/mole | | 0.06 | 0.06 | 0.06 | 0.06 | 0.06 | 0.06 | 0.06 |
| WHSV $Hr^{-1}$ | | 2.0 | 2.0 | 2.0 | 2.0 | 2.0 | 2.0 | 2.0 |
| Reaction time Hrs | | 140 | 144 | 136 | 150 | 146 | 140 | 150 |
| Reaction product wt % | | | | | | | | |
| Benzene, toluene, xylene | | 0.21 | 0.19 | 0.18 | 0.18 | 0.22 | 0.21 | 0.23 |
| Chlorobenzene | | 0.49 | 0.52 | 0.50 | 0.45 | 0.56 | 0.54 | 0.64 |
| Chlorotoluene | | 1.01 | 0.80 | 0.77 | 0.90 | 0.82 | 0.77 | 1.04 |
| Dichlorobenzene | | 1.14 | 1.08 | 1.04 | 0.96 | 1.24 | 1.21 | 1.31 |
| Dichloroxylene | 1.13 | 2.46 | 2.42 | 2.40 | 2.32 | 2.63 | 2.59 | 3.07 |
| ΣCEB | 98.87 | 94.69 | 94.99 | 95.11 | 95.19 | 94.53 | 94.68 | 93.71 |
| DCT isomer ration wt % | | | | | | | | |
| 2,5-DCT/DCT | 45.03 | 39.07 | 38.60 | 38.72 | 38.19 | 38.90 | 38.32 | 38.52 |
| 2,6-DCT/DCT | 0.88 | 6.33 | 6.78 | 6.64 | 7.00 | 6.39 | 6.98 | 6.71 |
| 3,5-DCT/DCT | 11.26 | 12.59 | 12.70 | 12.63 | 12.65 | 12.68 | 12.77 | 12.56 |
| 2,4-DCT/DCT | 34.35 | 31.75 | 31.51 | 31.58 | 31.43 | 31.66 | 31.27 | 31.63 |
| 3,4-DCT/DCT | 3.84 | 4.74 | 4.85 | 4.86 | 5.10 | 4.80 | 5.00 | 4.98 |
| 2,3-DCT/DCT | 4.64 | 5.52 | 5.56 | 5.57 | 5.63 | 5.56 | 5.66 | 5.60 |

From Table 7, it can be seen that if the maximum diameter of secondary particles of the mordenite in the formed catalyst is smaller than 5 microns, the catalyst activity is high, and so the reaction temperature can be lowered. Furthermore, it can be seen that if the primary particles of mordenite are smaller than 0.2 micron in the longest axis, the catalyst is more excellent and that if the silica/alumina molar ratio of mordenite is 15 to 30, the catalyst is excellent.

Example 15

CEB Isomerization Reaction

The catalyst composition F (Example 11) was tested in CEB isomerization reaction, and the results are shown in Table 8 below.

| Evaluation of catalytic performance (CEB isomerization reaction) | | |
|---|---|---|
| Catalyst | Supplied raw material | F (Example 11) |
| Reaction conditions | | |
| Reaction temperature °C. | | 245 |
| Reaction pressure MPa-G | | 4.0 |
| H/DCT mole/mole | | 0.06 |
| WHSV $Hr^{-1}$ | | 1.3 |
| Reaction time Hrs | | 188 |
| Reaction product wt % | | |
| Low boiling point compounds | | 0.02 |
| Benzene | | 0.10 |
| Ethylbenzene | 0.21 | 0.38 |
| Chlorobenzene | 0.06 | 0.61 |

-continued

| Evaluation of catalytic performance (CEB isomerization reaction) | | |
|---|---|---|
| Catalyst | Supplied raw material | F (Example 11) |
| ΣCEB | 99.73 | 95.79 |
| High boiling point products | | 2.10 |
| CEB isomer ratio wt % | | |
| o-CEB/CEB | 53.13 | 31.96 |
| m-CEB/CEB | 8.70 | 48.12 |
| p-CEB/CEB | 38.17 | 19.92 |
| CEB recovery rate wt % | | 96.05 |

From table 8, it can be seen that the catalyst composition shows high activity in CEB isomerization reaction.

What is claimed is:

1. A method for isomerizing halogenated aromatics comprising contacting a catalyst composition comprising a zeolite selected for isomerizing halogenated aromatics, wherein said composition further comprises a formed catalyst having secondary zeolite articles each with a maximum diameter of 5 microns or less with halogenated aromatics.

2. An isomerization method comprising contacting halogenated aromatics containing 15 ppm or less of dissolved oxygen with a zeolite-containing catalyst.

3. The isomerization method according to claim 2, wherein before the halogenated aromatics are contacted with said zeolite-containing catalyst, said halogenated aromatics are treated by a treatment method selected from the group consisting of dissipation treatment, reduced pressure treatment and distillation treatment, to remove the dissolved oxygen.

4. The isomerization method according to claim 2, wherein the zeolite-containing catalyst is a catalyst composition comprising a zeolite selected for isomerizing halogenated aromatics, wherein said composition further comprises a formed catalyst having secondary zeolite articles each with a maximum diameter of 5 microns or less.

5. The isomerization method according to claim 3, wherein the zeolite-containing catalyst is a catalyst composition comprising a zeolite selected for isomerizing halogenated aromatics wherein, said composition further comprises a formed catalyst having secondary zeolite articles each with a maximum diameter of 5 microns or less.

* * * * *

UNITED STATES PATENT AND TRADEMARK OFFICE
CERTIFICATE OF CORRECTION

PATENT NO. : 6,781,021 B2
DATED : August 24, 2004
INVENTOR(S) : Kato et al.

It is certified that error appears in the above-identified patent and that said Letters Patent is hereby corrected as shown below:

Column 10,
Line 61, please insert the following paragraph:
-- A paste mixture was prepared from 30 g (dry base) of the zeolite powder obtrained in Example 1, 24 of alumina sol (containing 10 wt% of $Al_2O_3$, "Colloidal Alumina 200", from Nissan Kagaku), 3 g of alumina gel (containing 70 wt % of $Al_2O_3$ "Cataloid AP (C-10)", from Shokubai Kasei), and distilled water. The mixture was kneaded. During kneading , a proper amount of distilled water was added, while the kneaded state was observed. After kneading for about 2 hours, the paste was formed into pellets like noodles through a screen with 0.8 mm dia. holes which was dried overnight at 120ºC and then calcined at 500ºC for 1 hour. --

Column 18,
Line 55, please change "articles" to -- particles --.

Column 19,
Line 3, please change "articles" to -- particles --.

Column 20,
Line 3, please change "articles" to -- particles --.

Signed and Sealed this

Fifteenth Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,781,021 B2
DATED : August 24, 2004
INVENTOR(S) : Kato et al.

It is certified that error appears in the above-identified patent and that said Letters Patent is hereby corrected as shown below:

Drawings,
Figure 3, please change
"■ Dissolved Oxygen 0 ppm
● Dissolved Oxygen 40 ppm" to
-- ● Dissolved Oxygen 0 ppm
■ Dissolved oxygen 40 ppm -- (as shown on the attached page).

Signed and Sealed this

Twenty-sixth Day of April, 2005

JON W. DUDAS
*Director of the United States Patent and Trademark Office*